United States Patent [19]
Yamamuro et al.

[11] Patent Number: 5,104,981
[45] Date of Patent: Apr. 14, 1992

[54] PROCESS FOR PRODUCTION OF ALKYL GLYCOSIDE EXCELLENT IN HUE

[75] Inventors: Akira Yamamuro, Wakayama; Makoto Amau, Osaka; Tadaaki Fujita, Wakayama; Kiyoshi Aimono, Wakayama; Akio Kimura, Wakayama, all of Japan

[73] Assignee: Kao Corporation, Tokyo, Japan

[21] Appl. No.: 494,360

[22] Filed: Mar. 16, 1990

[30] Foreign Application Priority Data

Mar. 22, 1989 [JP] Japan .................................. 1-70143

[51] Int. Cl.$^5$ ............................ C07G 3/00; C07H 1/06
[52] U.S. Cl. ................................. 536/18.6; 536/18.5; 536/124; 536/127
[58] Field of Search ................ 536/18.6, 18.5, 127, 536/124

[56] References Cited

U.S. PATENT DOCUMENTS

| | | | |
|---|---|---|---|
| 3,565,885 | 2/1971 | Molotsky et al. | 536/18.6 |
| 4,483,979 | 11/1984 | Mao | 536/127 |
| 4,557,729 | 12/1985 | McDaniel et al. | 536/18.5 |
| 4,762,918 | 8/1988 | McDaniel et al. | 536/127 |
| 4,904,774 | 2/1990 | McDaniel et al. | 536/124 |
| 4,950,743 | 8/1990 | McCurry et al. | 536/18.6 |

FOREIGN PATENT DOCUMENTS 132043 1/1985 European Pat. Off. .
132046 1/1985 European Pat. Off. .
0338151 10/1989 European Pat. Off. .

Primary Examiner—Ronald W. Griffin
Assistant Examiner—Everett White
Attorney, Agent, or Firm—Sughrue, Mion, Zinn, Macpeak & Seas

[57] ABSTRACT

A process is disclosed for the production of an alkyl glycoside excellent in hue, which comprises (1) reacting a sugar with alcohol to obtain an alkyl glycoside reaction product containing an unreacted higher alcohol, (2) reacting the resulting product with a metal/hydrogen complex represented by formula (I)

$$M(BH_4)_x \qquad (I)$$

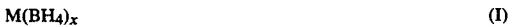

wherein
M is an alkali metal, Ca, Zn, or $(CH_3)_4N$; and x is 1 when M is an alkali metal or $(CH_3)_4N$ and x is 2 when M is Ca or Zn;

(3) separating the resulting reaction mixture into the alkyl glycoside and the unreacted higher alcohol, and (4) decomposing the remaining metal/hydrogen complex with an acid.

9 Claims, No Drawings

PROCESS FOR PRODUCTION OF ALKYL GLYCOSIDE EXCELLENT IN HUE

FIELD OF THE INVENTION

This invention relates to a process for the production of an alkyl glycoside. More particularly, it relates to a process for the production of an alkyl glycoside which is excellent in hue.

BACKGROUND OF THE INVENTION

An alkyl glycoside is a sugar derivative surfactant which is less irritating than other surfactants. Also, though it is a nonionic surfactant, alkyl glycosides form stable foam per se, and furthermore, exert a foam-stabilizing effect on other anionic surfactants. Recently, these characteristics have made alkyl glycosides highly noteworthy.

Although alkyl glycosides as novel surfactants have the above-mentioned noteworthy characteristics, it is quite difficult to produce them in the form of a commercially useful product.

The most serious problem in the production of alkyl glycosides is that various procedures during the production process thereof frequently cause deterioration of the hue of the product.

Thus, it has been attempted to prevent the deterioration of the hue of an alkyl glycoside during the production process, and some methods therefor have been proposed. For example, JP-A-59-139397 (the term "JP-A" as used herein means an "unexamined published Japanese patent application") discloses a process wherein a higher alcohol is reacted with a monosaccharide in the presence of an acid catalyst composition comprising an acid catalyst and a reducing agent to thereby provide an alkyl glycoside; European Patent 0132043 reports a process wherein an acid form of an anionic surfactant in the form of an acid is used as a catalyst; and European Patent 0132046 discloses a process wherein neutralization with an organic base is conducted at the termination of a reaction. Furthermore, JP-A-62-192396 discloses a process wherein a viscosity depressant is added upon the separation of the formed alkyl glycoside from the unreacted and recovered alcohol, since the high viscosity and poor heat stability of the alkyl glycoside would cause the particularly serious deterioration of the hue. However, none of these known processes can provide an alkyl glycoside having satisfactory hue for commercial practice.

JP-A-47-16413 (corresponding to U.S. Pat. No. 3,565,885) describes a process wherein an alkyl glycoside reaction product is contacted with a basic anion exchange resin prior to the separation so as to provide an alkyl glycoside having excellent hue; in this case, however, there is a problem with respect to the evolution of an amine odor causing the deterioration of the alkyl glycoside reaction product with respect to odor.

Furthermore, JP-A-61-33193 (corresponding to U.S. Pat. No. 4,557,729) describes a process wherein the finally obtained alkyl glycoside product is bleached with hydrogen peroxide and sulfur dioxide. However, this process is a rather drastic measure, and it is accompanied by other problems such as the deterioration with respect to odor and poor stability upon storage.

In addition, JP-A-1-290692 (corresponding to U.S. Pat. No. 4,762,918) proposes a process for improving the color of a glycoside composition which comprises contacting a glycoside composition containing colored humin with a hydrogen source (for example, hydrogen, sodium borohydride), but the product is still deficient in hue (see Comparative Example 4 below).

Thus, there have been reported a number of methods for the production of an alkyl glycoside excellent in hue. However, each alkyl glycoside thus produced shows an unsatisfactory hue or suffers from deterioration with respect to odor. That is, none of the foregoing methods can provide an alkyl glycoside which is excellent in both hue and odor.

SUMMARY OF THE INVENTION

Under these circumstances, we have conducted extensive studies in order to produce an alkyl glycoside excellent in hue and odor. As a result, we have found that deterioration of the hue of an alkyl glycoside is caused by reducing sugars such as the unreacted glucose, the acidic component formed by the decomposition of these reducing sugars and furan derivatives contained in the alkyl glycoside reaction product. We have further found that these materials causing coloration may be readily reduced by contacting the alkyl glycoside reaction product containing these materials with a specific metal/hydrogen complex. We have further found that the separation of the alkyl glycoside after the above-mentioned treatment by, for example, distillation, does not bring about any deterioration of the hue of the alkyl glycoside, thus completing the present invention.

As indicated above, it is an object of the present invention to provide a process wherein an alkyl glycoside reaction product containing materials causing coloration is contacted with a specific metal/hydrogen complex, to thereby preliminarily remove the materials causing coloration before they are converted into color bodies upon heating.

In the process of JP-A-1-290692, on the other hand, an alkyl glycoside containing color bodies is bleached with a metal/hydrogen complex such as sodium borohydride after removing the unreacted alcohol. Accordingly, the present invention is distinguished from that of JP-A-1-29062, e.g., in that the formation of color bodies is prevented before it happens.

Thus, in accordance with the present invention, there is provided a process for the production of an alkyl glycoside excellent in hue, which comprises (1) reacting a sugar with alcohol to obtain an alkyl glycoside reaction product containing an unreacted higher alcohol, (2) reacting the resulting product obtained with a metal/hydrogen complex represented by formula (I)

$$M(BH_4)_x \qquad (I)$$

wherein
M is an alkali metal, Ca, Zn, or $(CH_3)_4N$; and x is 1 when M is an alkali metal or $(CH_3)_4N$ and x is 2 when M is Ca or Zn;

(3) separating the resulting reaction mixture into the alkyl glycoside and the unreacted higher alcohol, and (4) decomposing the remaining metal/hydrogen complex with an acid.

DETAILED DESCRIPTION OF THE INVENTION

The alkyl glycoside relating to the present invention may be obtained by a commonly known method. For example, it may be obtained either by directly reacting a sugar with a higher alcohol in the presence of an acid catalyst, or by preliminarily reacting a sugar with a lower alcohol (for example, methanol, ethanol, propanol, butanol) to thereby provide a lower alkyl glycoside, which is then reacted with a higher alcohol.

The higher alcohol to be used in the process of the present invention may be represented by formula (II)

$$RO(AO)_nH \qquad (II)$$

wherein

R represents a straight-chain or branched alkyl, alkenyl, or alkylphenyl group having from 6 to 22 carbon atoms;

A represents an alkylene group having from 2 to 4 carbon atoms; and n indicates mean value and is a number equal to 0 to 5.

Specific examples of the higher alcohol represented by formula (II) include a straight or branched alkanol such as hexanol, heptanol, octanol, nonanol, decanol, dodecanol, tridecanol, tetradecanol, pentadecanol, hexadecanol, heptadecanol, octadecanol, methylpentanol, methylhexanol, methylheptanol, methyloctanol, methyldecanol, methylundecanol, methyltridecanol, methylheptadecanol, ethylhexanol, ethyloctanol, ethyldecanol, ethyldodecanol, 2-heptanol, 2-nonanol, 2-undecanol, 2-tridecanol, 2-pentadecanol, 2-heptadecanol, 2-butyloctanol, 2-hexyloctanol, 2-octyloctanol, 2-hexyldecanol and 2-octyldecanol; an alkenol such as hexenol, heptenol, octenol, nonenol, decenol, undecenol, dodecenol, tridecenol, tetradecenol, pentadecenol, hexadecenol, heptadecenol and octadecenol; and alkylphenols such as octylphenol and nonylphenol. These alcohols or alkylphenols may be used either alone or a mixture of two or more of them. Further, an alkylene oxide adduct of these alcohols or alkylphenols can be used.

The sugar to be used as the starting material for the production of the alkyl glycoside according to the present invention may be selected from monosaccharides, oligosaccharides, and polysaccharides. Examples of the monosaccharides include aldoses such as allose, altrose, glucose, mannose, gulose, idose, galactose, talose, ribose, arabinose, xylose, lyxose. Examples of the oligosaccharides include maltose, lactose, sucrose and maltotriose. Examples of the polysaccharides include hemicellulose, inulir, dextrin, dextran, xylan, starch and hydrolyzed starch. After the completion of the acetalization, some portion of these sugars used as the starting materials would remain in an unreacted form.

In the present invention, the production of an alkyl glycoside may be conducted with the use of the above-mentioned starting materials under known conditions (for example, catalyst, temperature) as disclosed, for example, in JP-B-47-24532 (the term "JP-B" as used herein means an "examined Japanese patent publication") (corresponding to U.S. Pat. No. 3,598,865), U.S. Pat. No. 3,839,318, European Patent No. 092355, JP-A-59-139397, and JP-A-58-189195.

Examples of the metal/hydrogen complex of formula (I) to be used in the present invention include lithium borohydride, sodium borohydride, potassium borohydride, tetramethylammonium borohydride, calcium borohydride and zinc borohydride. Among these substances, sodium borohydride is particularly preferable.

The metal/hydrogen complex represented by formula (I) to be used in the present invention may be added to the alkyl glycoside reaction product either as such (i.e., in the form of a powder) or in the form of an aqueous solution or an alkaline aqueous solution. The amount of the metal/hydrogen complex to be added generally ranges from 0.5 to 100 mole equivalents, and preferably from 2 to 20 mole equivalent, with respect to the reducing sugars dissolved in the alkyl glycoside reaction product. The treatment with the metal/hydrogen complex may generally be conducted at from 10° to 100° C., and preferably from 20° to 80° C. This treatment generally requires from 0.25 to 5 hours, and preferably is from 0.5 to 2 hours.

Finally, the excessive metal/hydrogen complex remaining in the system is decomposed with an acid, to thereby complete the treatment. Examples of the acid include sulfuric acid and p-toluenesulfonic acid.

Thus, the materials causing coloration (for example, reducing sugars) remaining in the alkyl glycoside reaction product may be readily reduced.

The foregoing may be confirmed by gas chromatography, showing, for example, that glucose is reduced into sorbitol.

After treating the alkyl glycoside reaction product containing the unreacted higher alcohol with the metal/hydrogen complex, the alkyl glycoside is separated from the unreacted higher alcohol to thereby give the alkyl glycoside excellent in hue. The separation of the alkyl glycoside from the unreacted higher alcohol may be conducted by any known method, such as distillation, without limitation.

To further illustrate the present invention, and not by way of limitation, the following Examples are provided. Unless otherwise indicated, all percents are by weight.

EXAMPLE 1

(a) 3460 g of decyl alcohol, 789 g of anhydrous glucose and 11.7 g of p-toluenesulfonic acid monohydrate were heated and stirred in a 10 liter flask. After heating the mixture to 100° C., the pressure in the system was reduced to 40 mmHg so as to initiate dehydration, while blowing nitrogen gas into the reaction mixture at a rate of 0.12 Nm$^3$/h to thereby efficiently remove the water thus formed. The amount of the glucose dissolved in the reaction mixture was determined by occasional sampling. 7.5 hours after the initiation of the reaction, the amount of the dissolved glucose reached 600 ppm. Then the reduced pressure was relieved, and the reaction mixture was neutralized with an aqueous solution of NaOH. The polysaccharides formed as by-products were filtered out, to thereby provide 4000 g of a reacted filtrate in which 450 ppm of glucose was dissolved.

(b) Next, 1 g of sodium borohydride was added to 1000 g of the reacted filtrate and the mixture was stirred at 70° C. for one hour. After cooling, the mixture was neutralized with an aqueous solution of p-toluenesulfonic acid to thereby adjust the pH value thereof to 7. Thus 0 ppm of glucose was dissolved in the filtrate thus treated.

800 g of the treated filtrate was distilled at 180° C. under 0.3 mmHg to thereby provide 210 g an alkyl glycoside (recovered decyl alcohol: 590 g).

EXAMPLE 2

The filtrate obtained in Example 1-(a) was treated in the same manner as described in Example 1-(b), except that the sodium borohydride was replaced with 1.7 g of calcium borohydride. After distilling the filtrate at 180° C. under 0.3 mmHg, 208 g of an alkyl glycoside (recovered decyl alcohol: 592 g) was obtained.

COMPARATIVE EXAMPLE 1

The filtrate obtained in Example 1-(a) was distilled at 180° C. under 0.3 mmHg, to thereby provide 212 g of an alkyl glycoside (recovered decyl alcohol: 588 g).

EXAMPLE 3

(a) The procedure of Example 1-(a) was repeated except that the decyl alcohol and anhydrous glucose were replaced with tetradecyl alcohol and galactose respectively. Thus, an alkyl glycoside containing unreacted tetradecyl alcohol was obtained.

(b) Next, the procedure of Example 1-(b) was repeated except that the sodium borohydride was replaced with potassium borohydride. Thus, an alkyl glycoside was obtained.

COMPARATIVE EXAMPLE 2

The filtrate obtained in Example 3-(a) was distilled at 190° C. under 0.3 mmHg to thereby obtain an alkyl glycoside.

EXAMPLE 4

(a) 3707 g of butanol, 903 g of anhydrous glucose and 4.7 g of p-toluenesulfonic acid monohydrate were heated under reflux in a 10 liter flask for 3 hours while distilling off the water thus formed. Then the reaction system became uniform and the formation of butyl glycoside was confirmed. After adding 3950 g of decyl alcohol, the pressure in the reaction system was slowly lowered to 40 mmHg at 115° to 120° C., and the butanol was distilled off. 4 hours after the addition of the decyl alcohol, the reduced pressure was relieved, and the reaction mixture was neutralized with a cooled aqueous solution of NaOH. Thus, 3900 g of the reacted mixture, in which 400 ppm of glucose was dissolved, was obtained.

(b) Next, 1 g of sodium borohydride was added to 1000 g of the reacted mixture and the obtained mixture was stirred at 70° C. for 1 hour. After cooling, it was neutralized with an aqueous solution of sulfuric acid to thereby adjust the pH value thereof to 7. The mixture thus treated contained 0 ppm of the dissolved glucose.

800 g of the treated mixture was then distilled at 180° C. under 0.3 mmHg, to thereby provide 200 g of an alkyl glycoside (recovered decyl alcohol: 600 g).

COMPARATIVE EXAMPLE 3

The reacted mixture obtained in Example 4-(a) was distilled at 180° C. under 0.3 mmHg, to thereby provide 201 g of an alkyl glycoside (recovered decyl alcohol: 599 g).

TEST EXAMPLE 1

The hues of the alkyl glycosides obtainer in Examples 1 to 4 and Comparative Examples 1 to 3 were compared before, immediately after and 4 days after the distillation. Table 1 summarizes the results.

The comparison was conducted by preparing a 25% (solids content) solution of each alkyl glycoside, and comparing the hues of these solutions by Gardner's method. A smaller Gardner value indicates better hue.

An organoleptic evaluation showed that the alkyl glycosides obtained in Examples 1 to 4 had no odor.

TABLE 1

| Alkyl glycoside | Hue (Gardner) | | |
|---|---|---|---|
| | Before* distillation | Immediately** after distillation | 4 days** after distillation |
| Example 1 | 2 | 2 | 2 |
| Example 2 | 2 | 2 | 2 |
| Comparative Example 1 | 2 | 7 | 7 |
| Example 3 | 2 | 2 | 2 |
| Comparative Example 2 | 2 | 7 | 7 |
| Example 4 | 4 | 4 | 4 |
| Comparative Example 3 | 4 | 8 | 8 | notes;
*The hue of the alkyl glycoside containing the unreacted alcohol in an amount of 75% by weight.
**The hue of the 25% by weight alkyl glycoside aqueous solution.

Table 1 indicates that the present invention provides a process for the production of an alkyl glycoside which suffers from no deterioration of the hue before and after distillation and has good hue and odor characteristics.

COMPARATIVE EXAMPLE 4

The alkyl glycoside was discolored by the process described in JP-A-1-290692, except that the amount of sodium borohydride to be added was changed to the amount used in Example 1.

Namely, 200 g of an aqueous solution containing 100 g of the alkyl glycoside of Comparative Example 1 was completely mixed with 4.2 g of a 14N solution of caustic soda containing 12% by weight of sodium borohydride. After allowing the mixture to stand at room temperature for 4 days, the alkyl glycoside thus obtained was diluted to 25% aqueous solution and it showed a hue (Gardner) of G 7.

As described above, the desired aqueous solution of the alkyl glycoside excellent in hue was not obtained by the process as described in JP-A-1-290692 in which the alkyl glycoside was treated with sodium borohydride in the state of an aqueous solution of which the unreacted higher alcohol has been distilled off.

Table 1 and Comparative Example 4 suggest that the present invention provides a process for the production of an alkyl glycoside which suffers from no deterioration before and after distillation and has a good hue and a good odor.

While the invention has been described in detail and with reference to specific examples thereof, it will be apparent to one skilled in the art that various changes and modifications can be made therein without departing from the spirit and scope thereof.

What is claimed is:

1. A process for the production of an alkyl glycoside excellent in hue, which comprises (1) reacting a sugar with alcohol to obtain an alkyl glycoside reaction product containing an unreacted higher alcohol, (2) reacting the resulting product with a metal/hydrogen complex represented by formula (I):

$$M(BH_4)_x \qquad (I)$$

wherein
M is an alkali metal, Ca, Zn or $(CH_3)_4N$; and x is 1 when M is an alkali metal or $(CH_3)_4N$ and x is 2 when M is Ca or Zn;
(3) decomposing the remaining metal/hydrogen complex with an acid and (4) separating the resulting reaction mixture into the alkyl glycoside and the unreacted higher alcohol.

2. A process for the production of an alkyl glycoside excellent in hue as in claim 1, wherein the alkyl glycoside reaction product is obtained by reacting said sugar with a higher alcohol.

3. A process for the production of an alkyl glycoside excellent in hue as in claim 1, wherein the alkyl glycoside reaction product is obtained by first reacting said sugar with a lower alcohol, and then reacting the product obtained with a higher alcohol.

4. A process for the production of an alkyl glycoside excellent in hue as in claim 1, wherein said metal/hydrogen complex of formula (I) is sodium borohydride.

5. A process for the production of an alkyl glycoside excellent in hue as in claim 1, wherein the amount of metal/hydrogen complex is from 2 to 20 mol equivalent with respect to the reducing sugars dissolved in the alkyl glycoside reaction product.

6. A process for the production of an alkyl glycoside excellent in hue as in claim 1, wherein the acid is at least one selected from the group consisting of sulfuric acid and p-toluenesulfonic acid.

7. A process for the production of an alkyl glycoside excellent in hue as in claim 1, wherein the treatment is conducted at a temperature of from 10° to 100° C. for a period of from 0.25 to 5 hours.

8. A process for the production of an alkyl glycoside excellent in hue as in claim 7, wherein the treatment is conducted at a temperature of from 20° to 80° C. for a period of from 0.5 to 2 hours.

9. A process for the production of an alkyl glycoside excellent in hue as in claim 8, wherein said metal/hydrogen complex of formula (I) is sodium borohydride.

* * * * *